(12) United States Patent
Kling

(10) Patent No.: US 7,037,300 B2
(45) Date of Patent: May 2, 2006

(54) METHOD OF PRODUCING A DIFFERENTIALLY STRETCHED MEMBER AND A DIFFERENTIALLY STRETCHED MEMBER PRODUCED THEREBY

(75) Inventor: Robert Kling, Skene (SE)

(73) Assignee: SCA Hygiene Products AB, Göteborg (SE)

(*) Notice: Subject to any disclaimer, the term of this patent is extended or adjusted under 35 U.S.C. 154(b) by 261 days.

(21) Appl. No.: 10/403,016

(22) Filed: Apr. 1, 2003

(65) Prior Publication Data
US 2004/0013850 A1    Jan. 22, 2004

Related U.S. Application Data

(60) Provisional application No. 60/368,979, filed on Apr. 2, 2002.

(51) Int. Cl.
*A61F 13/49* (2006.01)

(52) U.S. Cl. ............... 604/385.24; 156/160; 156/163; 156/164; 156/229; 428/98; 428/190

(58) Field of Classification Search ............... 156/160, 156/163, 164, 229; 428/98, 190; 604/385.24
See application file for complete search history.

(56) References Cited

U.S. PATENT DOCUMENTS

| 4,261,782 A | * | 4/1981 | Teed ........................... 156/164 |
| 4,300,562 A | | 11/1981 | Pieniak |
| 4,464,217 A | | 8/1984 | Dickover et al. |
| 4,525,407 A | * | 6/1985 | Ness ........................... 156/229 |
| 4,606,964 A | * | 8/1986 | Wideman ..................... 156/164 |
| 4,854,989 A | * | 8/1989 | Singheimer .................. 156/161 |
| 5,928,211 A | * | 7/1999 | Gustafsson et al. ......... 156/163 |
| 6,313,372 B1 | | 11/2001 | Suzuki |

FOREIGN PATENT DOCUMENTS

| EP | 0027303 A1 | 4/1981 |
| EP | 0556749 A1 | 8/1993 |
| EP | 0703068 A2 | 3/1996 |
| WO | 91/04724 A1 | 4/1991 |
| WO | 01/87213 A1 | 11/2001 |

* cited by examiner

*Primary Examiner*—Jeff H. Aftergut
(74) *Attorney, Agent, or Firm*—Buchanan Ingersoll PC (57) ABSTRACT

A method of producing an elasticized member having two different degrees of stretch, to be used in an absorbent product. The method involves stretching an elastic member by a first amount and securing part of it in the stretched condition to an inelastic web, while a second portion of the elastic member is stretched by a second amount and secured in the stretched position to the first web or to a second web. Differentially stretched products produced by the method can be used to provide advantages in terms of material savings and elasticity effects in absorbent products.

23 Claims, 7 Drawing Sheets

METHOD OF PRODUCING A DIFFERENTIALLY STRETCHED MEMBER AND A DIFFERENTIALLY STRETCHED MEMBER PRODUCED THEREBY

CROSS-REFERENCE TO RELATED APPLICATIONS

This application claims priority under 35 U.S.C. §119 to U.S. Provisional Application No. 60/368,979, filed on Apr. 2, 2002.

FIELD OF THE INVENTION

The present invention relates to a method of producing a differentially stretched member, such as a differentially stretched elongated strip, for use in an absorbent product (such as a diaper or the like for absorbing human exudate). In particular, the invention relates to a method of producing a differentially stretched member for use in the waist area of such an absorbent product.

BACKGROUND OF THE INVENTION

There is often a desire to provide a part of an absorbent product with differing degrees of elastic extension. For example, in the waist region a strip of elastic material is often placed between the top and back sheet having been given a pretension of some 30 to 80%, in order to provide an elasticized waist portion. Similarly, elastic side flaps, with a high degree of elasticity (i.e. able to be extended by a large distance elastically) and including an attachment means at the outer end of each flap, may be provided on one waist portion of an absorbent product for releasable attachment to a second waist portion.

The presence of an elasticized waist and elasticized side flaps requires differing elastic material portions to be handled and applied in a series of manufacturing operations. As a solution to this inconvenience, a single elastic strip member of high elasticity may instead be used to span across both the waist and end flaps, whereby the entire waist band and the end flaps are both imparted with a high degree of elasticity. However, since the waistband is not normally stretched to the available extent of this high degree of elasticity, the waist band material where the elastic strip member is attached will generally comprise very coarse gathers. The presence of these coarse gathers may affect either the comfort and/or the containment characteristics of the product. Additionally, when a highly stretched elastic material is attached in the waistband, a greater amount of material is required in the top sheet and/or back sheet in order to produce any given size of waist area, since the coarse gathers require a significant amount of top sheet and/or back sheet material.

The invention seeks to overcome the above problems, whereby individual areas of an absorbent product can be provided with differing degrees of elasticity such that differing areas can be stretched elastically by differing amounts, without resorting to the use of different elastic members in the different areas of the product.

WO-A-01/87213 discloses elasticated areas such as leg or waist areas, added to absorbent products. The elasticated areas are formed as laminates, in which a nonwoven elastic material is stretched and then fixed between two outer layers of inelastic material. The resulting laminate is provided with regions of differing elastic tension or in other words differing elastic modulus. This can be achieved for example by using elastic filaments which are separated by a different distance in two different parts of the laminate, or by using a different elastomeric polymeric compounds or mix of elastomers for the filaments in one part of the web compared to another part, or even by choosing different diameter filaments in different parts of the web. The filaments for the different areas of the web are passed over a common series of rollers in order to be stretched by a certain amount before being attached. In this way, all filaments are stretched the same distance. The resulting differently formed areas of the laminate may each be stretched, by different maximum forces up to the maximum extension of the non-elastic material, which thereby provides different characteristics in the same laminate.

Although the resulting laminate in WO-A-01/87213 includes areas of different elastic modulus, this does not concern the problem of providing areas of different elastic strain in a single member.

SUMMARY OF THE INVENTION

These and other objects are achieved by providing a method of producing a member which has been differentially stretched, and a product produced thereby.

In accordance with embodiments of the invention, an elastic member is used in combination with at least one relatively inelastic member.

An elastic member, such as a continuous or discontinuous sheet, web, layer, or net for example, is considered to be elastic in accordance with the invention if it can be elastically extended by more than 50% without substantial permanent strain, whereby substantial permanent strain is understood as being of the order of more than about 10 to 30% of the initial length at the first stretching. In most cases, elastic materials used in accordance with embodiments of this invention will have an elastic extensibilty of more than 100%, more preferably more than 200% or even more preferably more than 300%, and still more preferably more than 400%. Elastic members suitable for the invention may include for example, non-exclusively, elastomers made from block copolymers such as polyurethanes, copolyetheresters, polyamide polyether block copolymers, EVAs (ethyl-vinyl-acetates), elastomeric styrene-butadiene copolymers, tetrablock copolymers, including styrene-poly(ethylene-propylene) elastomeric block copolymers, polyamides, or natural and synthetic rubber materials, etc. One suitable elastomer is Extraflex™ CEX 802WR having a surface weight of 54 g/m², available from Tredegar film products.

Relatively inelastic members may comprise a continuous or discontinuous sheet, web, layer or fabric for example, which member can be stretched elastically by only small amounts, normally of the order of between 1 to 15%, but typically less than 10%.

A differentially stretched member is produced by applying different extension forces to different parts of an elastic member, preferably a uniform elastic member such as a film or net of homogenous material, or by applying the same extension forces to non-homogenous and/or non-uniform parts of an elastic member, before attachment of said elastic member to at least one relatively inelastic member. The resulting differentially stretched member may be a laminate or other layered structure, for example a substantially non-elastic sheet of an absorbent product attached to an elastic member. The differentially stretched member structure will thus comprise at least two portions, in series, the portions having different elastic properties in terms of elastic strain, such that when the structure is subjected to opposed lateral extension forces, the structure will be able to be extended elastically by a different amount in one portion as compared to the other portion.

BRIEF DESCRIPTION OF THE DRAWINGS

The invention will now be explained in more detail with reference to certain non-limiting embodiments thereof and with the aid of the accompanying drawings, in which.

DETAILED DESCRIPTION OF PREFERRED EMBODIMENTS

Figure 1:
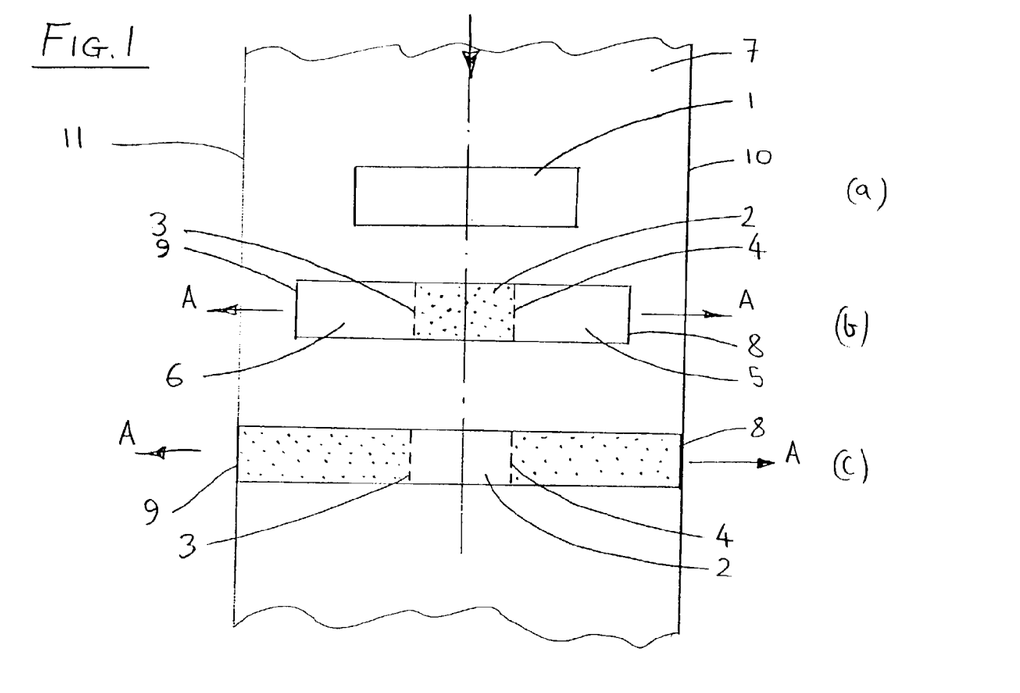
FIG. 1 shows a plan view illustrating the steps of a first embodiment of the invention.

In FIG. 1, an elastic member 1 in the form of an elongate rectangular strip, preferably of a uniform elastic material or possibly a net of uniform filaments, is placed above a first web 7. The first web is in the form of a continuous sheet of a relatively inelastic material. The member 1 thus has two major surfaces constituted by the upwardly facing surface in the Figure and the opposite lower surface. In step (a), the member 1 is laid flat on the first web 7 with one of its major surfaces overlying and preferably adjacent to the first web 7.

In step (b), the respective ends 8, 9 of the member 1 are each held by a suitable gripping means such as two sets of gripping jaws or gripping belts (not shown) of a manufacturing machine (not shown) and said gripping means are each moved outwardly in opposite directions respectively, as indicated by the opposed arrows A. In this way, the entire elastic member 1 is stretched into a first stretched condition. A suitable amount for this first stretched condition is an extension of e.g. between 30% and 80%, for example about 50%.

A first portion 2 of the elastic member is shown in FIG. 1 as extending between the upper and lower edges of the strip and between dashed lines 3 and 4. The first portion 2 is also positioned generally centrally with respect to the elastic member and also with respect to the first web 7, although off-centre arrangements (not shown) may be used.

The first portion 2 is maintained in the first stretched condition. This may be performed either by simply maintaining the gripping means at the initial extension or by the application of alternative means such as holding fingers (not shown) at, or outside of, lines 3 and 4, which will hold the first portion 2 in said first stretched condition.

In this maintained first stretched condition, the first portion 2 may now be fixedly secured to the underlying first web 7. Fixed securement may be carried out in any suitable manner such as by e.g. ultrasonic welding, heat welding, or by the use of adhesive (e.g. hot melt adhesive) applied preferably uniformly over the first portion 2 of member 1 between the first web 7 and the member 1.

With the first portion 2 maintained in said first stretched condition, each of the portions on either side of the first portion constitutes a second portion 5, 6 of the elastic member 1. In the next step, step (c), each of the gripping means mentioned above then moves further in the direction of the opposed arrows A so as to extend each of said second portions 5 and 6 by a second amount which is greater than said first amount. The second amount may for example be a stretch of each of the second portions of the elastic member (compared to an unstretched condition of said second portions) by an amount of up to 100% when the first portion has been stretched by up to 30%, or by an amount up to 200% when the first portion has been stretched by up to 60%, or up to 300% when the first portion has been stretched by up to 100%, or by up to 500% when the first portion has been stretched by up to 150%. As shown in FIG. 1, the ends 8 and 9 have been stretched suitably to coincide substantially with the outer edges 10, 11 of the first web 7.

In the condition shown, each of the two second portions 5, 6 is securely fixed to the first web 7 by any suitable method, such as those described above with reference to securely fixing the first portion 2 to the web 7. Preferably the same method is used to fixedly secure the first portion 2 and the second portions 5, 6 to the first web 7.

Although in the aforegoing embodiment the secure fixing of the first portion 2 to the first web 7 precedes the fixing of the second portions 5, 6 it is also possible to keep the first portion in said first stretched condition while stretching said second portions to said second stretched condition and only then fixedly attach the first web 7 to the first portion 2 and to the second portions 5, 6. Thus the first portion 2, although preferably attached to the first web 7 before the second portions 5, 6 can also be attached at the same time as the second portions are attached to the first web 7, or the first portion 2 could be attached after the second portions 5, 6 have been attached.

FIG. 1 shows the web 7 as a continuous web having a width (left to right in the Figure) equal to the width of the finally stretched elastic member 1 but with a greater height (top to bottom in the Figure). In such an embodiment, the differentially stretched strip formed at the end of step (c) may be cut from the continuous first web 7 at a cutting station (not shown). It will also be clear that, particularly for mass production, the elastic members 1 may be applied consecutively, or in groups, to the underlying web 7, with little or no gaps between consecutive elastic members 1.

In a still further embodiment, the elastic member may instead be formed as a continuous elastic web (i.e. like web 7) or in the form of an elastic web having a net structure, and the various operations shown in steps (a), (b) and (c) would be carried out sequentially during forward movement of both elastic and non-elastic webs such that a differentially stretched web comprising the combined web 7 and the elastic member web is formed. To use the combined web as a differentially stretched member in absorbent products, a cutting stage (not shown) would then be required before adding to the absorbent product.

Embodiments are also envisaged where the first web 7 is however shorter and generally corresponds to the height dimension (top to bottom as shown in the Figure) of elastic member 7 when in its stretched condition such that little or no trimming is required.

Although only a first web 7 is shown attached to one major surface of the elastic member 1, it should be understood that a second web (not shown), for example a second relatively inelastic web, preferably of the same material as the first web, may be applied to the other major surface of the elastic member 1. In such an embodiment, the operations of fixed securement of the first and second portions in the respective first and second stretched conditions should be carried out such that both the first and second webs are fixedly attached to the elastic member 1 at each securement operation. In this way, the elastic member becomes affixed or laminated between the first and the second webs.

The first and/or second web is preferably made of an inelastic nonwoven material. A typical nonwoven web may be made in the form of a spunbonded PP (polypropylene) fabric or an S-M-S (spunbond-meltblown-spunbond) fabric for example. Further examples are other types of spunbonded nonwovens or other nonwoven materials such as carded material, or material manufactured in another way. The nonwoven material can for example be made of synthetic fibres such as polyolefins, for example polypropylene or polyethylene. Other fibres such as for example different types of polyesters or nylon are also possible. It is further possible to use bi-component fibres and/or fibre mixtures of two or more different fibre types. One specific example of a nonwoven for use with the invention is a spunbonded nonwoven of polypropylene fibres having a basis weight of 12–30 g/m$^2$ and a fibre thickness of 0.5–5 dtex. Other nonwoven fabrics or webs may also be used.

Since the differentially stretched strip members are to be used in absorbent products, the relatively inelastic material should clearly be chosen to be soft, at least on the surface intended to contact the wearer's skin, and preferably on both surfaces.

Figure 2:
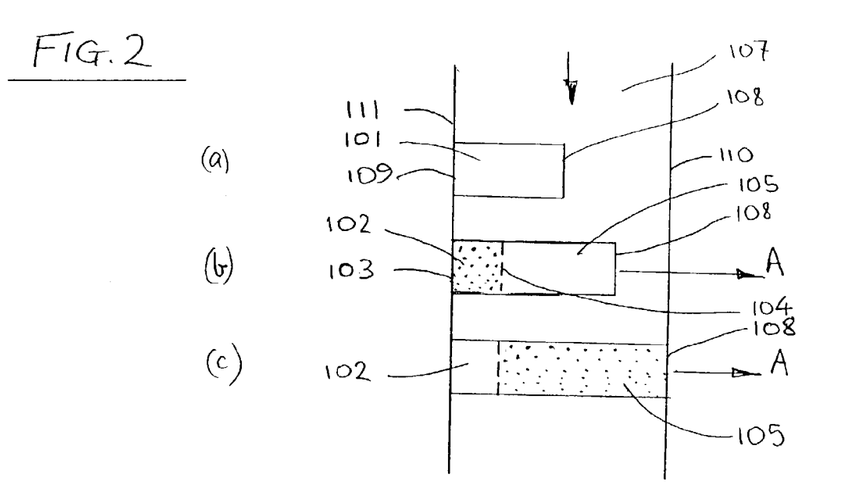
FIG. 2 shows a plan view illustrating the steps of a of a second embodiment of the invention.

In a second embodiment shown in FIG. 2, parts similar to those in the first embodiment have the same reference numerals raised by 100.

The differentially stretched strip of the second embodiment is produced in a manner similar to the strip of the first embodiment, but the final product only has one second portion 105. In step (a), the elastic member 101 is thus placed above and adjacent the first web 107.

In step (b), the elastic member 101 can be held stationary at its left edge 109 while the opposite edge 108 is gripped by suitable means (not shown) such as those described in the first embodiment. The gripping means are then moved in the direction of arrow A so as to stretch the entire elastic member by a first amount, said amount preferably being about 30 to 80% of the initial unstretched length of the elastic member 101. A first portion 102 is designated, said first portion extending from edge 109 to dashed line 104 and bounded by the upper and lower edges of the elastic member 101.

The first portion is then maintained in said first stretched condition and then attached fixedly to the underling web, whereby edge 109 of the elastic member is aligned with the edge 111 of the first web 107.

In step (c), the single second portion 105, positioned to the right of the first portion 102, is stretched in the direction of arrow A by a second amount which is different to and preferably greater than the first amount, the second amount may for example be a stretch of the second portion of the elastic member (compared to an unstretched condition of same) of greater than 100%, for example 200%. In this stretched condition, the edge 108 of the second portion 102 is preferably aligned with the edge 110 of the first web 107.

The second portion 102 is then fixedly secured, by any suitable means such as welding, adhesive or the like, to the first web 107.

The materials used in the first embodiment are equally applicable to use in the second embodiment and further embodiments, as are the attachment methods employed and the order of the steps in which fixed securement takes place.

Figure 11:
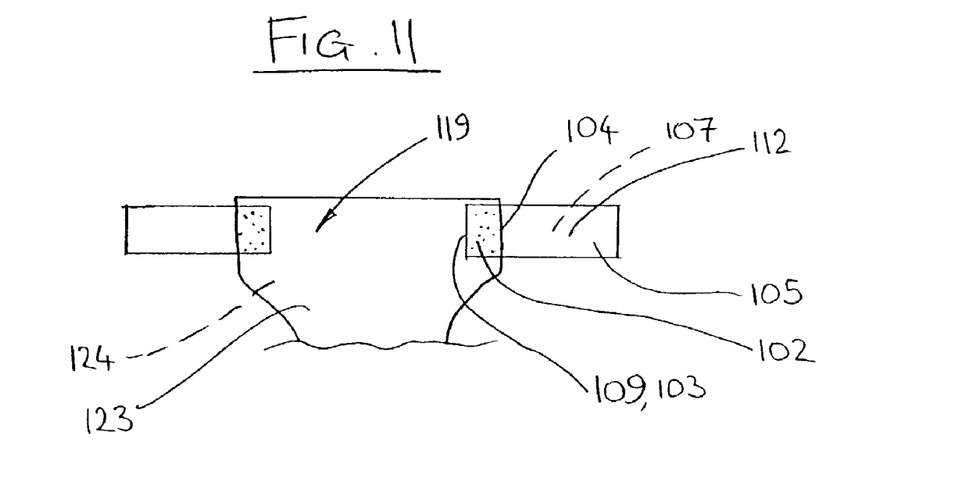
FIG. 11 shows a pair of strips, each made in accordance with the second embodiment, and each attached to respective side edge portions of an absorbent product.

A suitable area of use for the differentially stretched strip of the second embodiment is as a waist side flap of an absorbent diaper, whereby the first portion 102 of said differentially stretched strip is attached to one edge of an absorbent product and the second portion 105 extends from one edge of said absorbent product. FIG. 11 shows an example of such an attachment.

Figure 3:
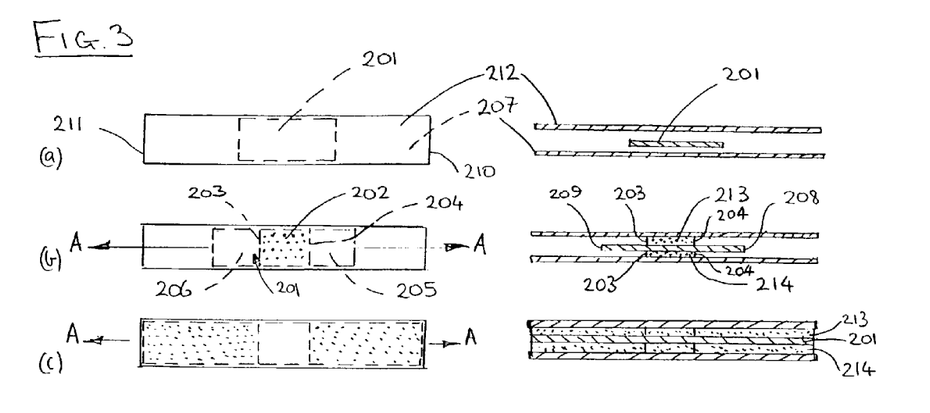
FIG. 3 shows a plan view and cross-sectional views illustrating the steps of a third embodiment of the invention, FIGS. 4a and 4b respectively show a plan view and cross-sectional view of a differentially stretched member in a relaxed condition.

In a third embodiment of the invention, shown in FIG. 3, a method of producing a differentially stretched belt having a first web and a second web is shown. Cross-sectional views of the elements in each stage are shown to the right in FIG. 3, whereby the thickness dimensions of the cross-sectional views are oversized for reasons of clarity. In this third embodiment, elements similar to those in the first embodiment have reference numerals raised by 200. Thus, in step (a), the respective major surfaces of the elastic member 201 are placed over and adjacent a relatively non-elastic first web 207 and underneath and adjacent a second web 212 respectively.

In step (b), the elastic member 201 is stretched by a first amount in a similar way to that described with respect to the first embodiment, by the order of about 30% to 80%. The elastic member 201, and thereby a first portion 202 having left and right imaginary boundaries 203, 204 shown in dashed lines, is maintained in said first stretched condition and said first portion 202 is fixedly secured to said first web 207 and to said second web 212. In the embodiment shown, attachment areas 213, 214 are shown positioned between the second web 212 and the first portion 202 and between the first web 207 and the first portion 202. Said attachment areas may for example be constituted by an adhesive which has been pre-coated on the surface of the elastic member 201 and/or the first and second webs 207, 212, whereby the adhesive may be activated by the use of heat applied through the area bounded by dashed lines 203, 204. Alternatively, the attachment areas 213, 214 may be regarded as being a weld, or other fixed attachment, between the elastic member and the first and second webs respectively.

In step (c), two second portions 205, 206 of the elastic member 201 are each stretched by a second amount, e.g. of the order of 100% or more. In the shown embodiment, the second portions 205, 206 are stretched such that their outer edges 208, 209 each are generally aligned with the outer edges 210, 211 of the first web 207 and the second web 212. However it will be evident that the elastic member 201 may also be stretched to an amount such that its outer end edges lie outside the end edges 210, 211.

The second portions are then secured fixedly to the first and second webs 207, 212 respectively while said second portions 205, 206 are still in said second stretched condition. A similar method of attachment as used for attachment of the first portion 202 to the first and second webs 207, 212 may be used.

Figures 4, 4A:
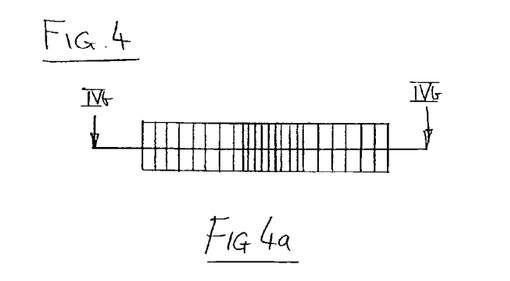
Figure 4B:
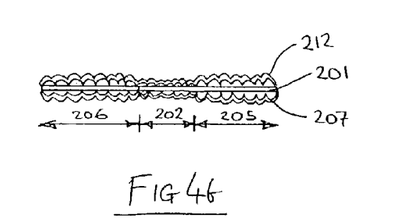

When the differentially stretched strip is released from the gripping means it assumes a relaxed state and has the shape of a rectangular strip as shown in FIG. 4a in plan view, whereby said elastic element has returned generally back to its initial length, although it is generally slightly longer due to some permanent elongation of the elastic material. FIG. 4a and FIG. 4b are however drawn on a different scale to FIG. 3 so as to more clearly indicate the gathers. FIG. 4b shows a cross-sectional view on to line IVb—IVb in FIG. 4a. In FIG. 4a and FIG. 4b, it can be seen that the first portion 202 and the second portions 205, 206 have each drawn the relatively inelastic first and second webs 207, 212 into a gathered condition by different amounts, whereby coarse gathers are present on the two second portions 205, 206 and fine gathers are present on the first portion 202. The coarseness of the gathering may of course also be affected by the actual pattern of binding sites between the elastic and non-elastic webs.

Figure 5:
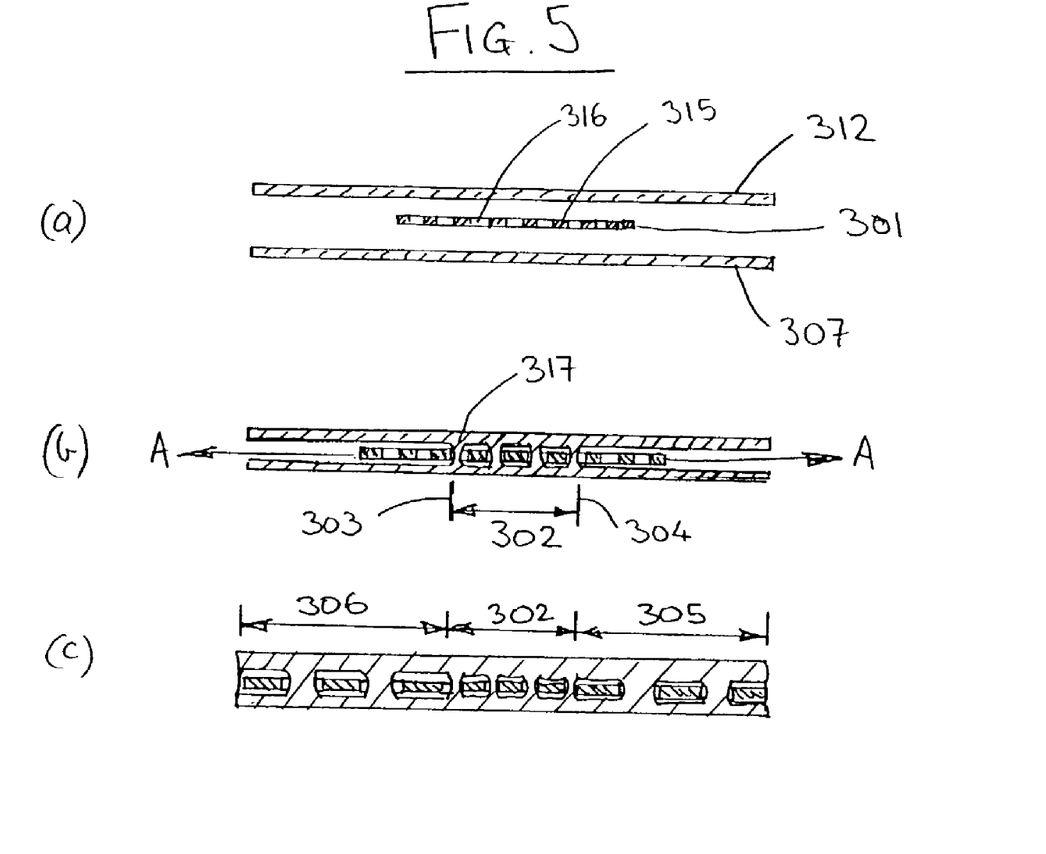
FIGS. 5a–5c show cross-sectional views through a differentially stretched member in the form of a net undergoing production.

FIG. 5 shows a further embodiment of the invention in cross-sectional view, not to scale, whereby the elastic member 301 is in the form of a net of elastic material. The net has longitudinal and laterally extending elastic material strands 315 surrounding apertures 316. Apertures 316 may be, for example, square or rectangular in shape. The cross-sectional shape of the elastic net members is shown as rectangular, but may be any suitable shape such as square, oval, circular, or any other shape.

In step (a) the elastic 301 member is placed between two relatively inelastic first and second webs 307, 312 and then stretched in mutually opposite directions denoted by arrows A, as explained with reference to the aforegoing embodiments.

As shown in step (b), a first portion 302 of the elastic member 301 located generally at the middle of the first and second webs 307, 312 is fixedly secured by means of the first and second webs 307, 312, by means of weld areas 317, such as ultrasonic weld areas, or adhesive or the like, whereby the first web 307 is connected to the second web 312 directly through the apertures 316 in the net, over preferably all the area of the first portion bounded by imaginary lines 303, 304.

In step (c), the net is stretched by a second, greater amount, such that the ends of the net generally extend up to the ends of the first and second web. In this stretched condition, the second portions 305, 306 of the elastic member are fixedly secured to respective outer portions of the first and second webs 307, 312 for example by welding or adhesive.

Although a net is used as the elastic member 301 in FIG. 5, the elastic member could equally be a continuous elastic film (not shown) without pre-formed apertures. The two webs 312 and 307 could however still be joined by means of e.g. ultrasound welding through the elastic film, thereby creating apertures in said film where webs 312 and 307 are joined. Alternatively, adhesive may be used for example.

Figure 6:
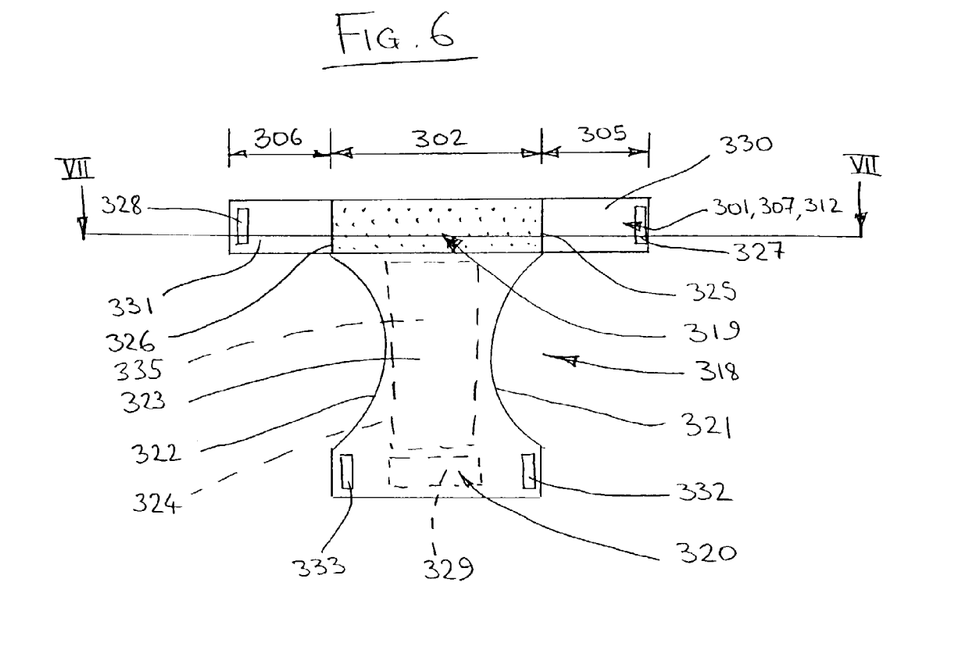
FIG. 6 shows a plan view of a differentially stretched band attached to an absorbent product in the waist region thereof.

FIG. 6 schematically shows an absorbent diaper 318, typically comprising a top sheet 323 and back sheet 324 surrounding an absorbent core 335 which could comprise cellulose fluff or other absorbent material, optionally mixed with superabsorbent gelling material. The diaper 318 has two opposed ends, each comprising a waist portion 319, 320 including the top sheet 323 and the back sheet 324 and optionally a part of the absorbent core. Between each waist portion there are curved leg openings 321, 322. Additional features such as standing gathers and elastics of various types may also be fitted in the longitudinal direction of the diaper. Such additional features are well known in the art.

Further, a differentially stretched member 301, 307, 312 in the form of a rectangular strip (shown as a single element) has been fixed to the upper end waist portion 319, whereby the first portion 302 together with its attached first and second webs 307, 312 can be initially stretched to its elastic limit (i.e. the first amount of stretching) and then fixedly attached in a relatively flat condition to the top sheet 323 and/or to the back sheet 324 which are also in a relatively flat condition. The second portions lie outside the outer edges 325, 326 of the waist portion 319 formed by the top and back sheets 323, 324.

When allowed to relax, the absorbent product gathers the waist region 319 as the first portion 302 returns to its relaxed length. Each of the outer portions 330, 331 (i.e. second portions 305, 306 with attached first and second webs 307, 312) of the differentially stretched member is fitted with an attachment means 327, 328 respectively. Said attachment means 327, 328 can for example releasably attach to a corresponding member 329 on the outer surface of the opposite waist portion 320 in a stretched condition of said outer portions 330, 331, such that the members 327, 328 and 329 respectively together form a releasable attachment means, for example of the mechanical type provided with cooperating hook and loop type fasteners (e.g. Velcro®), or the like.

Alternatively, only one of the members 327 or 328 need be present on one outer portion, for example in the form of a strip 327 of hook-type material of a hook and loop type fastener, or other similar mechanical fastener, whereby the two outer portions 330, 331 can be passed around a user's waist and the attachment strip 327 is engaged in the outer surface of outer portion 331 to thereby secure the outer portions 330, 331 together in the form of a belt. Attachment means such as hook-type attachment strips 332, 333 on the top sheet 323 may then be used to fix the front waist part 320 of the absorbent product to the waist belt formed by the connected portions 330, 331.

Although the portion 302 has been shown substantially equal in lateral extent to the extent of the top and back sheets in FIG. 6 such that the outer portions 330, 331 start at the edges 325, 326 of the top and back sheets 323, 324 in the waist portion 319, it is to be understood that this is only exemplary and the outer portions 330, 331 may start laterally inside the outer edges 325, 326, or they may start laterally outside the outer edges 325, 326. Additionally, the first portion 302 and its attached webs 307, 312 do not need to be attached to the top and/or back sheets over the whole area (as indicated by the dotted area in FIG. 6), but instead may be attached over a smaller area (e.g. over only a central portion of the top and/or back sheet in the waist portion 319 lying inside the edges 325, 326). Thus, for example the first portion need only be attached to the waist region 319 over a distance of between 25% and 75% of the distance between the edges 325, 326 for example. As a further example, the first portion may be attached to the waist region all the way along the upper edge (i.e. the outermost edge) of the depicted dotted area of same but not at the lowermost edge in a middle portion, such that in this way an inwardly open pocket can be formed having lines of connection proximate the outer edge and proximate the edges 325, 326. Such a pocket can be used for holding exudate and thus improving leakage resistance.

Figure 7:
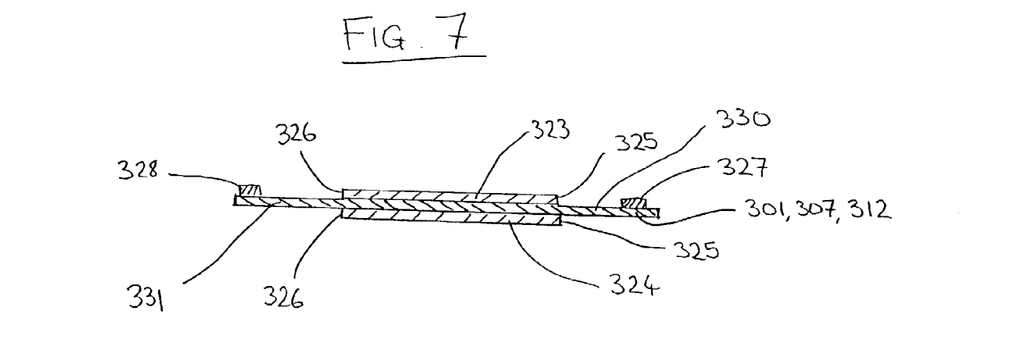
FIG. 7 shows a cross-sectional view on to line VII—VII in FIG. 6.

FIG. 7 shows a cross-sectional view along line VII—VII in FIG. 6, wherein the differentially stretched member comprising the elastic member 301 combined with first and second webs 307, 312, is shown as a single layer sandwiched between, and fixedly attached to, the top sheet 323 and back sheet 324 of the absorbent product.

Figure 8:
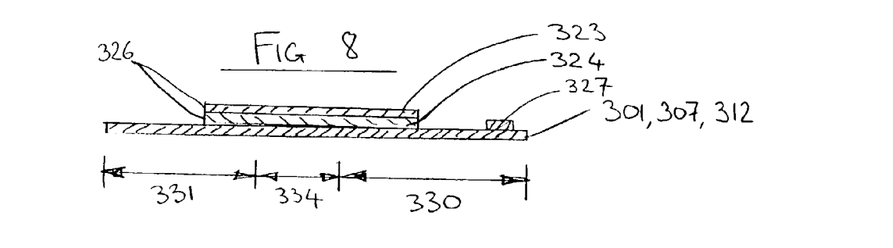
FIG. 8 shows a cross-sectional view similar to FIG. 7 of an alternative embodiment.

FIG. 8 shows an alternative embodiment, similar to FIG. 7, wherein the differentially stretched strip member comprising layers 301, 307, 312 is affixed to the outer surface of the back sheet 324. The attachment may be made over the whole area of contact of the back sheet 324 with the differentially stretched member, or only over part of the area, such as over an area having length 334. The top sheet 323 and the back sheet 324 are joined directly. In this embodiment, the outer portions 330, 331 of the differentially stretched member start inside the edges 325, 326 of the top and back sheets 323, 324 and the middle portion 334 corresponds to the part of the differentially stretched member containing the first portion 302.

Figure 9A:
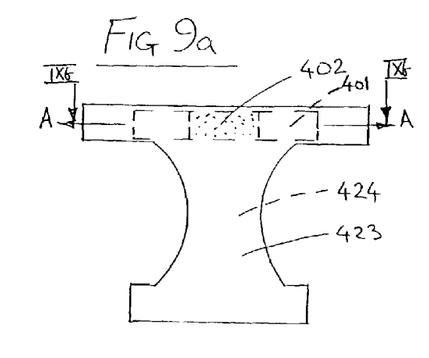
FIGS. 9a–9d show a plan view and sectional views of a further embodiment of the invention whereby the top sheet and back sheet are used as first and second relatively inelastic webs.
Figure 9B:
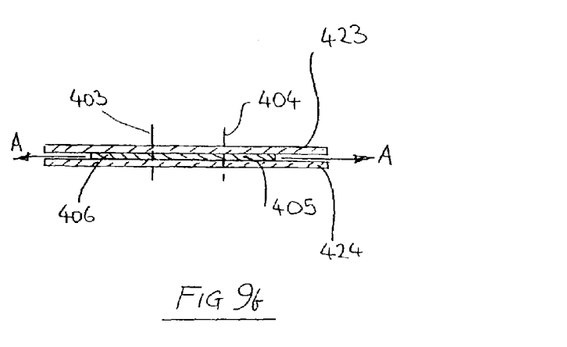
Figure 9C:
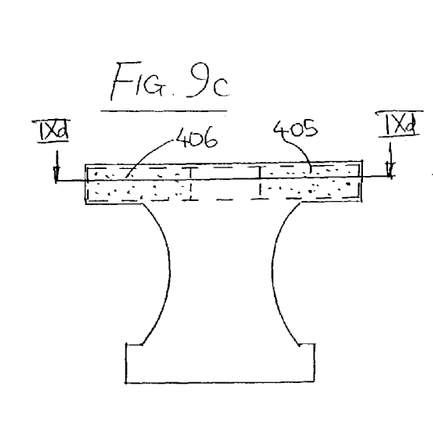
Figure 9D:
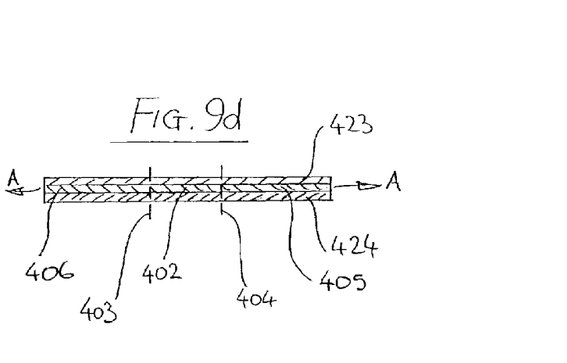

FIG. 9*a* and FIG. 9*c* show two different stages of production in plan view, while FIG. 9*b* shows a cross-sectional view on to line IXb—IXb and FIG. 9*d* shows a cross-sectional view on to line IXd—IXd in FIG. 9*c*.

In FIG. 9*a* top sheet 423 is attached to a back sheet 424 in a similar way to that shown in FIG. 6. However, the embodiment of FIG. 9 and FIG. 6 differ in that in FIG. 9 both the top sheet 423 and back sheet 424 are used to sandwich an elastic member 401 therebetween. Thus the differentially stretched member is formed of three parts, the top sheet 423 as a first relatively inelastic web, the back sheet 424 as a second relatively inelastic web and an elastic member 401.

In accordance with the earlier described methods, the elastic member 401 is stretched in opposing directions indicated by arrows A by a first amount and then a first portion 402 is fixed securely to the top sheet 423 and/or back sheet 424 by suitable means as described previously, such as by ultrasonic welding for example. In the shown embodiment, the elastic member 401 is however fixed to both the top sheet 423 and the back sheet 424. Then, the two outer portions 405, 406 of the elastic member are stretched by a second greater amount so that their ends become aligned substantially with the outer ends of the top and back sheets 423, 424. Then the two second portions 405, 406 are secured in said extended condition to the top and back sheets 423, 424.

When allowed to relax (not shown), the first portion 402 will gather the central waist portion top and back sheets 423, 424 until the elastic member has returned substantially to its initial length in the first portion, and the two second portions 405, 406 will gather the top and back sheets 423, 424 by an additional amount. As a result, the central part of the waist band may then be stretched elastically by a first amount e.g. up to 50% to resume a relatively flat condition and the outer portions may be stretched elastically by a greater amount e.g. up to 150% or more.

Figure 10:
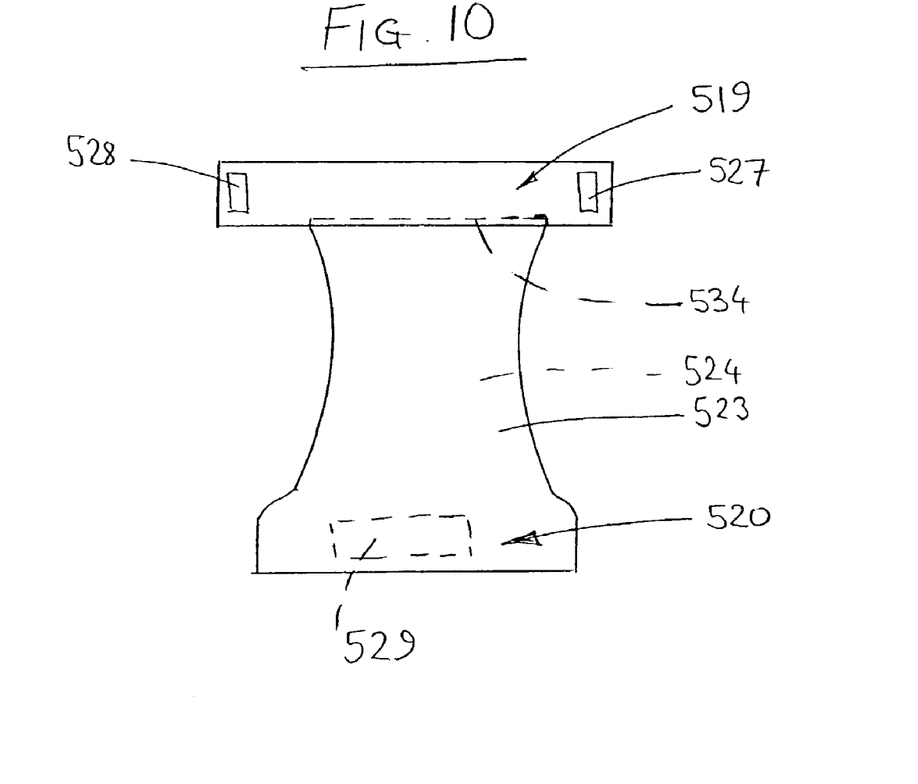
FIG. 10 shows a schematic plan view of a still further embodiment of the invention.

In the embodiment shown in FIG. 10, a differentially stretched member such as that resulting from the final step in the FIG. 1 embodiment, or the embodiments in FIGS. 4*a*–4*b*, and 5*a*–5*c* for example, is used to form one waist portion 519 of an absorbent product. The differentially stretched member is fixedly attached, e.g. by welding or adhesive or the like, to the upper end 534 of an absorbent product such as the absorbent product shown in FIG. 6 but without an upper waist portion formed by the top and back sheets 523, 524. Suitable releasable attachment means 527, 528 may be provided on the waist portion 519 to releasably attach to corresponding means 529 on the opposite waist portion 520 so as to be able to releasably attach the waist portions 519, 520 together.

FIG. 11 shows a top waist portion of an absorbent product formed by a top sheet 123 joined to a back sheet 124 with absorbent core (not shown) therebetween. In the waist region 119 thereof, a pair of differentially stretched members produced by for example the method shown in FIG. 2 are attached one to each side of the waist region 119. The attachment is such that the first portion 102 (together with the attached first web and second web) is attached to the top sheet 123 and/or the back sheet 124, whereby the outer edge 104 of said first portion is preferably aligned with an outer edge of said top sheet 123 and/or said back sheet 124. In such a way, a first degree of elastication is given to the waist region at the outer edges of the waist portion and a second higher degree of elastication is given to the flap members (i.e. those parts of the differentially stretched member extending outside the first portion 102).

Further embodiments will be readily understood by the skilled person upon reading the aforegoing and are intended to be encompassed within the scope of the invention as defined by the appended claims. For example, although the differentially stretched member has been described as a rectangular strip, other shapes of strip are also possible, such as oval.

Further, although a first portion and at least one second portion have been described, it should be understood that the invention can be applied to an elastic member having further portions, whereby one or more further portions may be located between the first and second portions, and/or outside the second portions, and the elastic member subject to at least one different, preferably larger, amount of stretching for each additional portion.

In the aforegoing description, the elastic member has been described as preferably comprising a uniform elastic web. However, the idea behind the invention may also be used with non-uniform elastic webs such as that depicted in FIGS. 12*a* and 12*b*, a non-uniform cross section elastic member 601 of substantially homogenous elastomeric material having a central first portion 602 and two second portions 605, 606 is shown positioned in an unstretched state between two relatively inelastic webs 607, 612.

Figure 12:
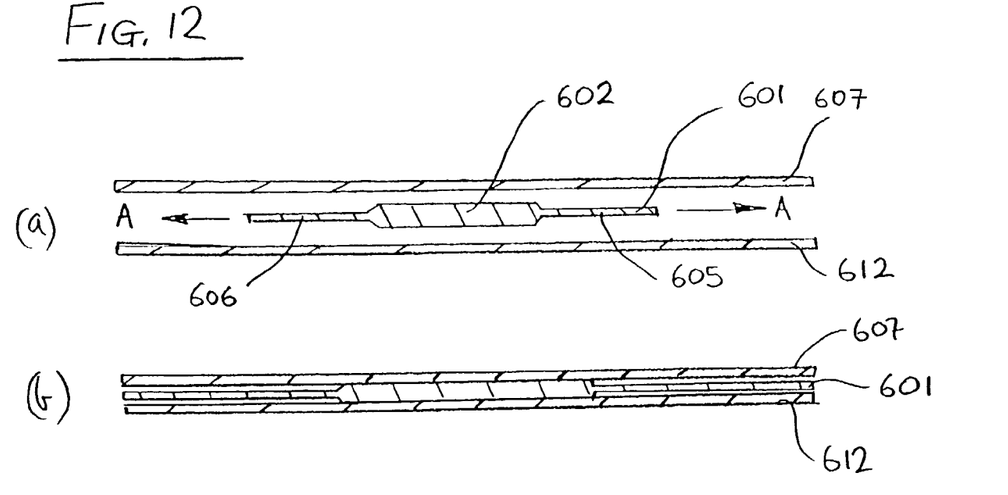
FIGS. 12a and 12b show cross-sectional views of a still further embodiment of the invention.

A single set of opposed forces in the direction of arrows A are applied to the elastic member 601 so that the outer ends of the elastic member 601 align approximately with the outer ends of the inelastic webs 607, 612. The outer ends of the elastic member 601 could however instead be extended further than the outer ends of the inelastic webs or not as far out as the outer ends of the inelastic webs. The elastic member 601 is then fixedly attached, by any suitable methods as described with respect to the aforegoing embodiments, to either or both webs 607, 612 at its first portion 602 and at both its outer portions 605, 606. In this way, a differentially stretched member can be produced without needing to apply two different extensions. As will be evident, the first portion 602 has been elongated over a shorter distance than the outer portions since it exhibits a greater modulus of elasticity, and thus the resultant strain is less on the central portion (i.e. the central portion is extended less compared to its original length than the outer portions). When the resulting laminate is then allowed to relax, the central part will cause a minimal gathering whereas the outer portions will gather more. When the laminate is stretched again, the central portion can only be stretched by a small distance elastically whereas the outer portions may be extended elastically a greater amount.

A further adjustment can be made in the embodiment described with respect to FIGS. 12*a* and 12*b* as described in the following. After the single force has been applied to stretch the entire elastic member 601 (for example such that the outer ends of the elastic member 601 lie outside the outer ends of the inelastic webs 607, 612), the first portion 602 can be fixedly attached to the inelastic webs 607, 612. Then the force stretching the elastic member in the direction of opposed arrows A is then reduced somewhat followed by subsequent attachment of the second portions to the webs 607, 612. In this way, a laminate is obtained which can be stretched to a maximum in the outer areas (corresponding to the second portions) before the central area has approached its maximal extension.

The different modulus of elasticity of the first portion 602 in FIGS. 12a and 12b as compared to portions 605, 606 can also be obtained in other ways such as for example by using a different polymer mix in these different portions, or by adding strengtheners or additional fibres or the like in the portion 602 compared to portions 605, 606.

The invention may be used as a waist belt or a waist band which is to be attached to a waist portion of a top sheet and/or back sheet of an absorbent product, or which is to form the waist portion of an absorbent product. The invention also relates to products resulting from said method. Further features of the invention will be apparent to the reader of this specification.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent diaper comprising a waist region extending laterally therein and provided with a differentially stretched member, said differentially stretched member comprising:
   an elastic member including at least a first portion and at least one second portion, and at least a first relatively inelastic web, said first web being in overlying contact with a first major surface of said elastic member;
   wherein said first portion and said at least one second portion are fixedly secured to at least said first web, wherein in the fixedly secured condition, said at one second portion is elastically extendable by a greater amount than said first portion in said lateral direction, and
   wherein said first portion is closer to the middle of said waist region than aid at least one second portion,
   wherein said at least one second portion comprises two second portions, one said second portion on either side of aid first portion, and
   wherein said second portions are aligned with said first portion along the lateral direction of said waist region.

2. The absorbent article according to claim 1, wherein in the fixedly secured condition said first portion is elastically extendable by up to 60% and said at least one second portion is elastically extendable by up to 200%.

3. The absorbent article according to claim 1, wherein a second relatively inelastic web is in overlying contact with a second major surface of said elastic member.

4. A differentially stretched waist member, comprising:
   an elastic waist member including at least a first portion and at least one second portion; and
   at least a first relatively inelastic web, said first web being in overlying contact with a first major surface of said elastic member,
   wherein said first portion and said at least one second portion are fixedly secured to at least said first web,
   wherein in the fixedly secured condition, said at least one second portion is elastically extendable by a greater amount than said first portion in a lateral direction, and
   wherein said at least one second portion comprises two second portions, one said second portion on either side of said first portion, and
   wherein said second portions are aligned with said first portion in the lateral direction thereof.

5. A differentially stretched member according to claim 4, wherein a second relatively inelastic web is in overlying contact with a second major surface of said elastic member, and wherein said first portion and said at least one second portion are fixedly secured to at least one of said first web and said second web.

6. A differentially stretched member according to claim 5, wherein at least one of said first web and said second web comprises a nonwoven fabric.

7. A differentially stretched member according to claim 4, wherein in the fixedly secured condition said first portion is elastically extendable by up to 60% and said at least one second portion is elastically extendable by up to 200%.

8. A method of producing a differentially stretched member for an absorbent product, comprising:
   stretching, in a stretching direction, an elastic member by a first amount to reach a first stretched condition;
   maintaining a first portion of said elastic member in said first stretched condition while the remainder of said elastic member is stretched by a second amount such that at least one second portion of said elastic member reaches a second stretched condition;
   providing a first relatively inelastic web adjacent a first major surface of said elastic member; and
   fixedly securing said first portion in said first stretched condition by means of at least said first web and thereafter fixedly securing said at least one second portion in said second stretched condition by means of at least said first web;
   wherein said first amount of stretching to reach said first stretched condition is between 30% and 80% of an initial length of the elastic member;
   wherein said second amount of stretching of said at least one second portion to reach said second stretched condition is greater than said first amount of stretching; and
   wherein said at least one second portion includes two second portions, said first portion lying between said two second portions, whereby said two second portions are aligned with said first portion in said stretching direction, and
   wherein said step of stretching said elastic member by a first amount to reach said first stretched condition is performed by applying a stretching force to each of said second portions in a direction of alignment of said first and second portions.

9. The method according to claim 8, further comprising:
   providing a second relatively inelastic web adjacent a second major surface of said elastic member, said elastic member being positioned between said first web and said second web; and
   fixedly securing said first portion in said first stretched condition by means between said first web and said second web and fixedly securing said at least one second portion in said second stretched condition by means of said first web and said second web.

10. The method according to claim 9, wherein said fixedly securing said first portion and said at least one second portion comprises securing said first web to said second web through said elastic member.

11. The method according to claim 9, wherein said fixedly securing said first portion and said at least one second portion comprises fixedly securing said first web to said elastic member and fixedly securing said second web to said elastic member.

12. The method according to claim 9, wherein said first web comprises a top sheet or back sheet of an absorbent product.

13. The method according to claim 9, wherein said first web or said second web comprises a top sheet or back sheet of an absorbent product.

14. The method according to claim 9, wherein said differentially stretched member is subsequently attached by means of at least an area corresponding to its first portion), to a waist area of an absorbent product, to thereby provide an elasticized waist belt for said absorbent product.

15. The method according to claim 9, wherein at least one of said first web and said second web comprises a nonwoven fabric.

16. The method according to claim 9, wherein at least one of the fixedly securing said first portion in said first stretched condition and the fixedly securing said at least one second portion in said second stretched condition is performed by ultrasound welding said elastic member between said first web and said second web.

17. The method according to claim 8, wherein the fixedly securing said first portion is performed before securing said at least one second portion.

18. The method according to claim 8, wherein said at least one second portion has an unstretched length, and wherein said second amount of stretching is greater than 100% of said unstretched length.

19. The method according to claim 18, wherein the second amount of stretching is between 100% and 200% of said unstretched length.

20. The method according to claim 18, wherein the second amount of stretching is between 200% and 300% of said unstretched length.

21. The method according to claim 8, wherein the maintaining said first portion in said first stretched condition while stretching the remainder of said elastic member is performed by fixedly securing said first portion to at least said first web.

22. The method according to claim 8, wherein said elastic member is provided in the form of a net.

23. The method according to claim 8, wherein said elastic member is provided in the form of a continuous elastic film.

* * * * *